United States Patent [19]
Klitmose

[11] Patent Number: 6,045,537
[45] Date of Patent: Apr. 4, 2000

[54] SYRINGE WITH AUTOMATICALLY WITHDRAWABLE OF PISTON ROD

[75] Inventor: Lars Peter Klitmose, Gentofte, Denmark

[73] Assignee: Novo Nordisk A/C, Bagsvaerd, Denmark

[21] Appl. No.: 08/973,109

[22] PCT Filed: Jun. 3, 1996

[86] PCT No.: PCT/DK96/00236

§ 371 Date: Dec. 2, 1997

§ 102(e) Date: Dec. 2, 1997

[87] PCT Pub. No.: WO96/38190

PCT Pub. Date: Dec. 5, 1996

[30] Foreign Application Priority Data

Jun. 2, 1995 [DK] Denmark ................................ 0625/95

[51] Int. Cl.[7] ............................................... A61M 5/315
[52] U.S. Cl. ............................................ 604/224; 604/234
[58] Field of Search ..................................... 604/207, 208, 604/209, 211, 232, 233, 234, 151, 155, 224; 222/325, 327

[56] References Cited

U.S. PATENT DOCUMENTS

| | | | |
|---|---|---|---|
| 3,110,310 | 11/1963 | Cislak | ...................................... 604/209 |
| 4,430,079 | 2/1984 | Thill et al. | . |
| 4,749,109 | 6/1988 | Kamen | ............................... 604/224 X |
| 4,988,337 | 1/1991 | Ito | ....................................... 604/224 X |
| 5,226,342 | 7/1993 | Panin | . |
| 5,637,095 | 6/1997 | Nason et al. | ......................... 604/224 X |

FOREIGN PATENT DOCUMENTS 0 064 858   11/1982   European Pat. Off. .
44 19 235 A1   12/1995   Germany .

OTHER PUBLICATIONS

Spec. of Pharma–Plast A/S, pp. 1–12.

Primary Examiner—Wynn Wood Coggins
Assistant Examiner—A. T. Nguyen
Attorney, Agent, or Firm—Steve T. Zelson, Esq.

[57] ABSTRACT

A syringe for injection of doses of a medicine from an exchangeable cartridge has a housing comprising a cartridge holder and a dosing mechanism by which a dose is set and injected by successively advancing a piston rod to press a piston into the cartridge. The dosing mechanism comprises a threaded spindle and a nut member cooperating with the spindle. A dose is set by relative rotation of the spindle and nut member whereby the nut member is moved along the spindle. The position of the nut member on the spindle defines how far the piston rod is advanced. The spindle and the nut are locked against relative rotation when the dosing mechanism is not operated to set a dose. Access to the cartridge holder is obtained by opening a lid connected to the housing and coupled to the dosing mechanism in such a way that the locking of the nut element in its position on the spindle is released when the lid is opened, and the opening movement of the lid is transmitted to a piston rod retraction mechanism.

7 Claims, 2 Drawing Sheets

SYRINGE WITH AUTOMATICALLY WITHDRAWABLE OF PISTON ROD

STATEMENT REGARDING FEDERALLY SPONSORED RESEARCH OR DEVELOPMENT

Not applicable

BACKGROUND OF THE INVENTION

CROSS-REFERENCE TO RELATED APPLICATIONS

The invention relates to syringes for dosed injection of a medicine from an exchangeable cartridge of the kind having a piston which is forced into a tubular cartridge to press out a dose of medicine corresponding to the movement of the piston, the syringe having a housing comprising a cartridge holder and a dosing mechanism by which a dose is set and subsequently injected by successively advancing a piston rod to press the piston into the cartridge, said dosing mechanism comprising a threaded spindle and a nut member co-operating with the spindle so that by setting of a dose relative rotation of the spindle and the nut member will move the nut member along the spindle, the position of the nut member on the spindle defining how far the piston rod is advanced during the injection, and the relative rotation of the spindle and said nut member being locked to keep the nut member in its position on the spindle when the dosing mechanism is not operated to set a dose.

To make a syringe as easy to handle as possible, the number of operation means should be minimized. Ideally the operation means only comprises a means for setting a dose and a means for injecting the set dose. Disposable syringes only comprising these two kinds of means are known, but if it is wanted to have a syringe which does not infer that the dosing mechanism is disposed of each time a cartridge integrated in such a pen is empty, the cartridge must be exchangeable. This infers that one more operation must be performed frequently as the cartridge must be changed when it is empty.

This in itself should cause no more complications than the fact that a new disposable syringe must be taken into use when the previous one is empty. However the syringe must be screwed apart to open access to the used cartridge and screwed together again when a new cartridge has been inserted. This is a mounting function by which care must be taken not to damage the threads by which the syringe is screwed apart and the screwing movement is difficult to perform when the tactile motor function is reduced.

Further, the medicine is pressed out of the cartridge by a piston which is pressed successively further into the tubular cartridge by the piston rod forming a part and the dosing mechanism. When the cartridge is empty said piston rod projects into the cartridge in almost the total length thereof. To change the cartridge the piston rod must first be drawn out of the empty cartridge, and thereafter it must be brought back to its initial position in the dose setting part. The last operation is made possible by locks getting unlocked when the empty cartridge is removed from the syringe, whereafter the piston rod may be pushed or screwed back to its initial position.

Although this retraction of the piston rod may seem to be simple, it infers a major risk for destroying the pen due to wrong handling as an attempt to press a piston rod which should have been screwed is just as destroying as screwing a piston rod which should have been pressed.

BRIEF SUMMARY OF THE INVENTION

It is the object of the invention to provide a syringe in which a cartridge may be changed without having to perform screwing movements, without having to take the syringe to pieces, and without having to pay attention to the piston rod and its retraction.

This is obtained by a syringe of the kind mentioned in the opening of this specification which syringe is characterised in that access to the cartridge holder is obtained by opening a lid connected to the housing and coupled to the dosing mechanism in such a way, that the locking of the nut element in its position on the spindle is released when the lid is opened.

The release of said locking may be obtained either by bringing the inner thread of the nut member out of engagement with the spindle or by allowing a free relative rotation of the nut member and the spindle. When the locking is released the nut member, which have during the injections performed been moved to a position on the spindle corresponding to a fully advanced piston rod, may be moved along the spindle back to its position corresponding to a totally retracted piston rod.

According to the invention the opening movement of the lid may further be transmitted to a piston rod retraction mechanism so that the piston rod is automatically withdrawn from the cartridge and the nut element is moved to its corresponding initial position when the lid is opened.

Further according to the invention the lid may be a slideable lid which gives access to the cartridge holder by being slided in the axial direction of the syringe. A piston rod retraction member may be rigidly connected to the lid and may engage means at the rear end of the piston rod to draw this piston rod and the nut member back to an initial position when the lid is slided in the axial direction of the syringe to give access to the cartridge holder. The piston rod retraction member may be provided with means engaging the dosing mechanism to release the locking of the nut element in its position on the spindle during the initial part of the sliding movement of the lid to have access to the cartridge holder. In this way the cartridge holder is made ready to receive a new cartridge when the lid is slided away to give access to the cartridge holder.

However, as only partly opening of the lid immediately may result in a partly withdrawal of the piston rod, it may result in an imprecise dosing if the lid is partly opened and then closed again. It is therefore appropriate to provide a detent mechanism which prevents the lid from being closed unless it has been fully opened as it may be practised as a well established habit that the pen must be made ready for use in the same way as when a new cartridge is mounted every time the lid has been opened.

The detent mechanism may comprise a finger on the lid, which finger resiliently engages a track in the syringe housing which track comprises a first and a second of parallel grooves so that the finger follows the first groove during the opening movement of the lid and the second groove during the closing movement of the lid, at least the first groove being provided with saw tooth detents which only allows the finger to be moved in the opening direction of the lid.

In another embodiment the detent mechanism may comprise a pawl mounted on a part rigidly connected to the lid and designed to engage a linear toothing in the housing, recesses being provided at each end of the toothing, which recesses allow the pawl to change its direction of detention.

In an embodiment the lid may be hinged to the syringe housing and the cartridge holder may follow the lid when swung out from the housing to give access to this cartridge holder from the front end thereof. In this embodiment the piston rod must either be retracted from the cartridge holder before this holder is swung away from its axial direction in relation to the rest of the syringe, or the piston rod must be flexible to allow it to be deflected with the piston holder. In this case a used cartridge is pulled out from the end of the cartridge holder leaving the piston rod extending axially in the holder but with the locking of the nut member in its position on the spindle is released. When a new cartridge is inserted from the end of the cartridge holder with its piston foremost the piston rod will automatically be pressed back and will bring the nut element back to its initial position when the cartridge is inserted. As the piston rod is surrounded by the cartridge holder, there is no risk that the user will try to screw it back.

BRIEF DESCRIPTION OF THE DRAWINGS

In the following the invention is described in further details with references to the drawing, wherein.

DETAILED DESCRIPTION OF THE INVENTION

Figure 1:
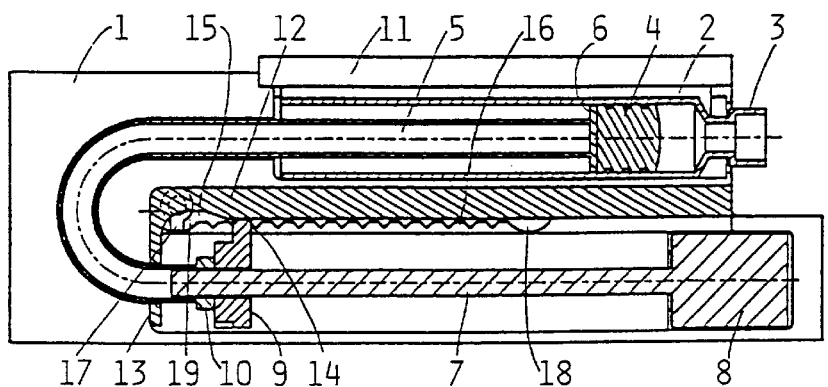
FIG. 1 shows schematically a sectional view of a syringe according to the invention with its lid closed and the cartridge empty ready for changing.

The syringe comprises a housing 1 accommodating in a compartment a cartridge 2 from which a medicament may be forced out through a needle (not shown) mounted at a neck part 3 of the cartridge 2 at one end thereof. The other end of the cartridge 2 is closed by a piston 4, and the medicament is forced out through the needle by forcing the piston 4 into the cartridge 2. The piston 4 is pressed by a piston rod 5 having a foot 6 abutting against the outer end of the piston.

In the showed embodiment the piston rod is flexible and is deflected 180° at the end of the cartridge. Thereby it is made possible to place the dose setting device next to the cartridge instead of in axial continuation of the cartridge as it is commonly seen.

The dose setting device is here schematically illustrated as a threaded spindle 7 which may be rotated by turning a knob 8 at one end of the spindle 7 the other end of which is rotatably guided in the piston rod which is hollow as it is made as a tight wound helix leaving a hole along its axis. When the spindle 7 is rotated a nut 9, which is mounted in the housing 1 in a way making it unrotatable relative to the housing but displaceable in the longitudinal direction thereof, will move along the spindle 7. When the nut 9 is moved towards the deflected end of the piston rod 5 it will press this end in and axial direction and this movement is transmitted through the deflected part of the piston rod, which is guided in a corresponding channel in the housing 1, to the other end of the piston rod 5 which will then force the piston 4 further into the cartridge 2. The piston rod end abutting the nut 9 is provided with an end cap 10 having a larger diameter than the piston rod 5.

The compartment accommodating the cartridge 2 is closed by a lid 11 which may be slided in the longitudinal direction of the syringe.

The lid 11 is connected to a connecting part 12 which is guided in an appropriate guideway in the housing 1 to ensure said longitudinal displacement in the direction towards the needle end of the cartridge 2. At its end opposite said needle end the connecting part 12 is provided with a carrier part 13 extending perpendicularly to the connecting part 12 and surrounds the deflected end of the piston rod 5 by a free fit allowing the piston rod 5 but not its end cap 10 to pass through an opening in the carrier part 13.

When the cartridge is empty as in FIG. 1, it have to be changed by a full one. To do this by the shown embodiment the lid is slided in the distal direction of the syringe that is in the direction towards the needle mounting end of the cartridge. By other embodiments of the syringe, e.g. the conventional form having the cartridge and the dose setting part placed in axial continuation of each other, it may be appropriate to have a lid which is slided in the proximal direction of the syringe.

When the lid is displaced to open the cartridge accommodating compartment the carrier part 13 of the connecting part grips behind the end cap 10 of the piston rod and pull this rod so that its end carrying the foot 6 is pulled out of the cartridge. When the compartment is opened totally, the piston rod 5 will also be drawn totally out of the cartridge which may then be removed and replaced by a new full one without any interference with the piston rod 5.

However, precautions have to be taken to make it possible to the carrier part 13 to move the nut 9 along the spindle 7. This is obtained by using a nut which is engaging the spindle in a releasable way. E.g. the nut may comprise two halves which moves away from each other to couple them free of the spindle unless they are kept together by an external pressure. In the schematic drawing this external pressure may be provided by the connecting part 12 abutting a locking part 14 of the nut. During the very first part of the sliding movement of the lid and the connecting part a recess 15 in the surface engaging the locking part 14 of the nut 9 is brought to a position abreast of the locking part 14 and consequently the engagement between the nut 9 and the spindle 7 is released and the nut may freely be moved along the spindle when the piston rod 5 is pulled back by the carrier part 13.

Figure 3:
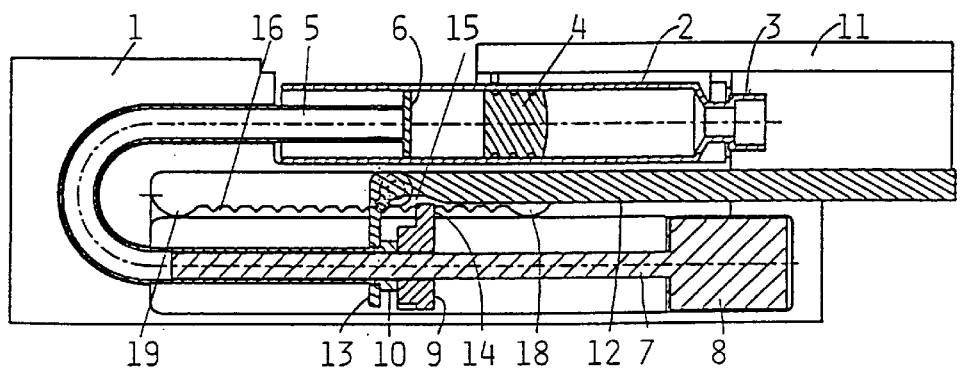
FIG. 3 shows a view corresponding FIG. 1 with the lid partly opened.
Figure 2:
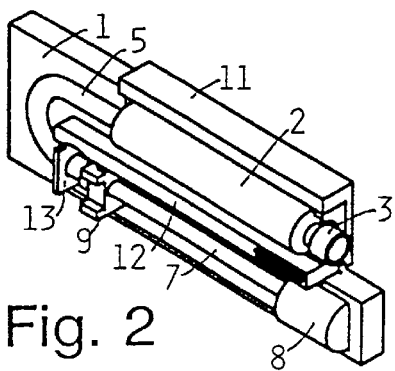
FIG. 2 shows in a reduced scale a 3-dimensional view of the part in FIG. 1.
Figure 4:
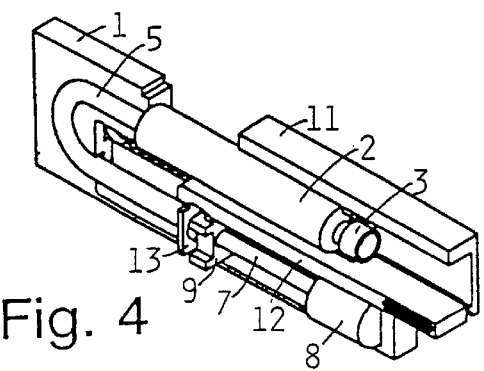
FIG. 4 shows in a reduced scale a 3-dimensional view of the part in FIG. 3.

FIG. 3 shows the syringe at a status during the opening of the compartment in which the cartridge is accommodated. The carrier part 13 is pulling the piston rod 5 out of the cartridge and is at the same time displacing the nut 9 along the spindle 7 in a direction towards the knob 8 all concurrently with the sliding of the lid to a position leaving free access to the compartment over the full length of an cartridge.

Figure 5:
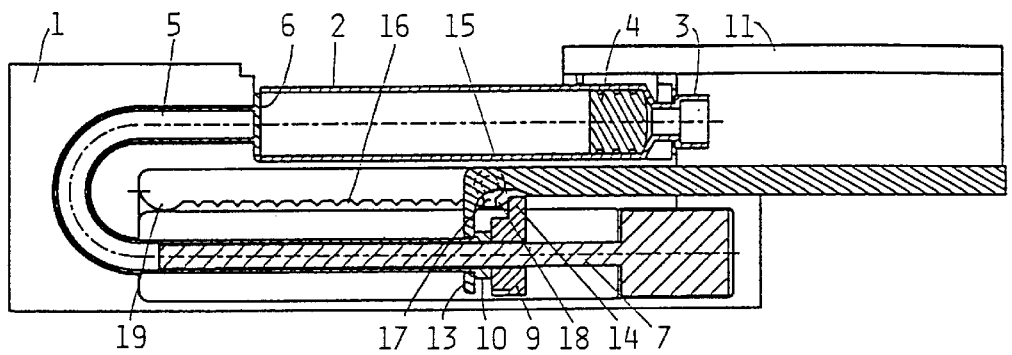
FIG. 5 shows a view corresponding to the views of FIGS. 1 and 3 with the lid fully opened.

FIG. 5 shows this full opened position for the lid. Now the empty cartridge may be removed and a new cartridge may be inserted without any interference with the piston rod which is drawn fully out of the compartment with its foot 6 forming an end wall of this compartment.

After a new cartridge has been placed in the compartment, the lid is slided back to its position closing this compartment. During the closing movement of the lid and its connecting part the carrier part 13 will slide along the piston rod without carrying along neither this rod nor the nut 9 abutting the end cap 10 of the piston rod. Very early during the closing movement of the lid the recess 15 in surface of the connecting part 12 is moved past the locking part 14 of the nut 9 and this locking part will now abut the not recessed part of the surface and keep the nut 9 in engagement with the thread of the spindle 7. Rotating the knob 8 in an appropriate direction will make the nut 9 move in a direction towards the end cap 10 of a first end of the piston rod 5 and this way force the second end of this piston rod into the cartridge in the compartment to press out the liquid content of said cartridge through a not shown needle mounted at the neck part 3 of said cartridge.

When a new cartridge is taken into use, the foot 6 through which the piston rod 5 influences the piston 4 is requested to be constantly abutting the piston 4 until the content of the cartridge is used and the cartridge is ready for changing. To avoid that the foot 6 of the piston rod is drawn partly back due to the lid being partly opened and thereafter closed again a mechanism is provided which ensures that when the lid is partly opened, it cannot be closed again without first being fully opened. This way an unaware partly opening and closing is avoided.

Figure 7:
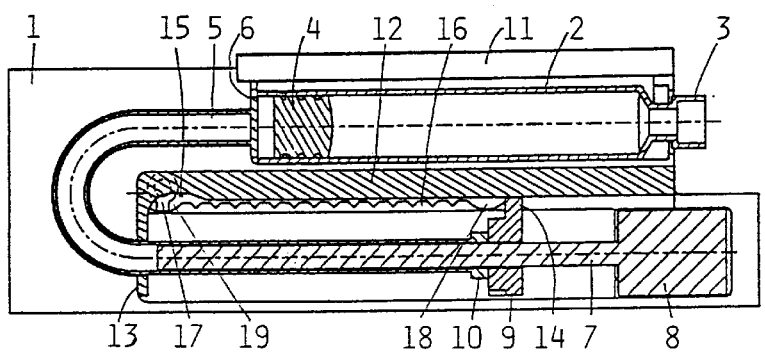
FIG. 7 shows schematically a view corresponding to the views in FIG. 1, 3, and 5 with the lid closed after a new cartridge has been loaded into the syringe.
Figure 6:
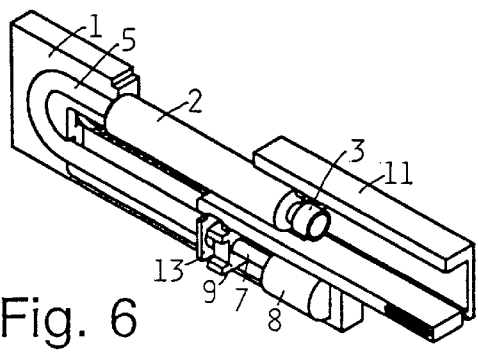
FIG. 6 shows in a reduced scale a 3-dimensional view of the part in FIG. 5.
Figure 8:
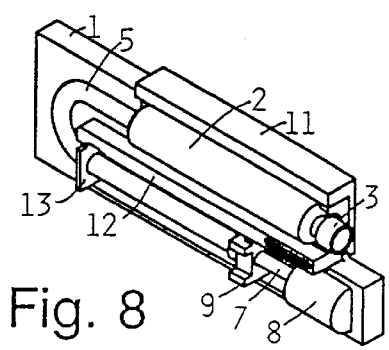
FIG. 8 shows in a reduced scale a 3-dimensional view of the part in FIG. 7

The mentioned mechanism comprises a toothing 16 in the housing 1 which toothing collaborates with a pawl 17 mounted on the connecting part 12. When an opening of the lid is initiated the pawl may click along the toothing as long as an opening movement is performed but if attempt is made to slide the lid in the closing direction, the pawl will bar this movement as it is seen in FIG. 3. When the lid is fully opened as shown in FIG. 5, the pawl will reach a recess 18 at an end of the toothing. This recess will allow the pawl to change is direction of blocking so that when a closing movement is initiated a renewed opening movement may only be initiated after the lid has been fully closed as the pawl now will block any movement in the opening direction until the pawl may turn its direction of blocking by entering a recess 19 at the other end of the toothing as is the case in FIG. 1 and 7. A not shown spring tends to force the pawl to a position perpendicular to the toothing.

In the above description the engagement between nut and spindle is described as releasable. Another way to make it possible to displace the nut along the spindle is to give the thread a pitch so that it is not self blocking i.e. so that the spindle will rotate when the nut is by force displaced along the spindle. The locking function released when an opening of the lid is initiated must then be provided by a lock preventing the spindle from rotating inadvertently during the use of the syringe.

Further the lid is shown as a slidable one. Also a hinged lid could be used when an appropriate coupling is established between the opening movement of the lid and the carrier moving the piston rod out of the cartridge. As mentioned also the syringe may be of a type having the dosing mechanism and the cartridge positioned end to end.

I claim:

1. A syringe for dosed injection of a medicine from a replaceable cartridge, said syringe comprising:
    a housing comprising a cartridge holder for receiving a replaceable cartridge of the type having a piston which can be forced into the cartridge to press out a dose of medicine;
    a lid coupled to the housing for movement between closed and open positions, wherein the lid, when in the latter position, provides access to the cartridge holder for changing cartridges; and
    a dosing mechanism including a piston rod moveable within the housing for administering doses of medicine from a cartridge; a threaded spindle; a nut member selectively engageable with the spindle so that relative rotation of the spindle and the nut member moves the nut member along the spindle; and a coupling mechanism for moving the piston rod during an injection a distance dependent upon the relative position of the nut member on the spindle; and wherein the lid is coupled to the dosing mechanism so that, when the lid is closed, relative movement between the spindle and nut occurs only when the nut member and spindle are rotated relative to one another and, when the lid is opened, the nut member can be moved relative to the spindle without relative rotation between the spindle and nut member.

2. A syringe according to claim 1, further comprising a piston rod retraction mechanism coupled to the lid for automatically moving the piston rod into a withdrawn position, responsive to opening the lid, to allow cartridges to be removed from, and mounted in, the cartridge holder.

3. A syringe according to claim 2, wherein the lid is mounted on the housing for sliding movement in an axial direction of the syringe.

4. A syringe according to claim 3, wherein the piston rod withdrawal mechanism includes a piston rod retraction member rigidly connected to the lid and having a engagement member engaging means engaging the piston rod to move the piston rod back into its withdrawn position the lid slides in the axial direction to provide access to the cartridge holder.

5. A syringe according to claim 4, wherein the piston rod retraction member has means engaging the dosing mechanism to release the nut element from engagement with the spindle during an initial part of the sliding movement of the lid when the lid slides in a direction to provide access to the cartridge holder.

6. A syringe according to claim 5, further comprising a detent mechanism coupled between the lid and the housing which prevents the lid from being closed unless it has first been fully opened.

7. A syringe according to claim 6, wherein housing has linear toothing with axially spaced recesses at either end thereof, wherein the detent mechanism comprises a pawl mounted on a part rigidly connected to the lid for engaging the toothing for one-way detention of movement, and wherein the recesses allow the pawl to change its direction of detention.

\* \* \* \* \*